United States Patent [19]

Dagenais et al.

[11] Patent Number: 4,664,959
[45] Date of Patent: May 12, 1987

[54] ABSORBENT BED PAD

[76] Inventors: J. Roger Dagenais, 438 Kindersley, Town of Mount Royal, Quebec; Jacques Dagenais, 1330 Seville Crescent, Brossard, Quebec; Paul Poirier, 917 Malo, St-Hilaire, Quebec, all of Canada

[21] Appl. No.: 597,092

[22] Filed: Apr. 5, 1984

Related U.S. Application Data

[63] Continuation of Ser. No. 334,665, Dec. 28, 1981, abandoned, which is a continuation of Ser. No. 154,433, May 29, 1980, abandoned.

[51] Int. Cl.⁴ .................. B32B 3/02; B32B 3/06; A61F 13/06
[52] U.S. Cl. .................. 428/74; 5/484; 5/500; 428/76; 428/102; 428/190; 428/192; 428/284
[58] Field of Search .............. 428/74, 76, 102, 190, 428/192, 284; 604/358, 375, 378, 383; 5/484, 500

[56] References Cited

U.S. PATENT DOCUMENTS

| | | | |
|---|---|---|---|
| 1,334,901 | 3/1920 | Higdon | 5/500 |
| 1,533,973 | 4/1925 | Cohen et al. | 5/484 |
| 1,569,955 | 1/1926 | Falter | 428/102 |
| 2,019,842 | 11/1935 | Bussing et al. | 604/378 |
| 2,660,735 | 12/1953 | Baum | 5/484 |
| 2,897,108 | 8/1959 | Harwood | |
| 3,427,670 | 2/1969 | Nimoy | 5/484 |
| 3,498,296 | 3/1970 | Gallagher | 604/378 |
| 3,528,421 | 1/1970 | Vaillancourt | 5/354 |

FOREIGN PATENT DOCUMENTS 528825 8/1958 Canada .
957801 11/1974 Canada .

Primary Examiner—Paul J. Thibodeau
Attorney, Agent, or Firm—Samuel Meerkreebs

[57] ABSTRACT

An absorbent pad for use on hospital beds, including an impervious sheet co-extensive with one or a pair of absorbent fabric sheets, the absorbent fabric sheets covering the supplemental liquid absorbent material in the center thereof and being stitched to the impervious layer about the periphery thereof.

3 Claims, 4 Drawing Figures

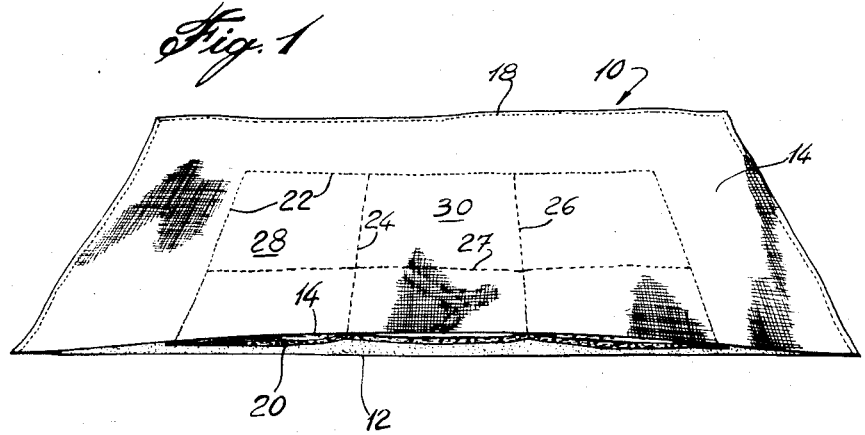
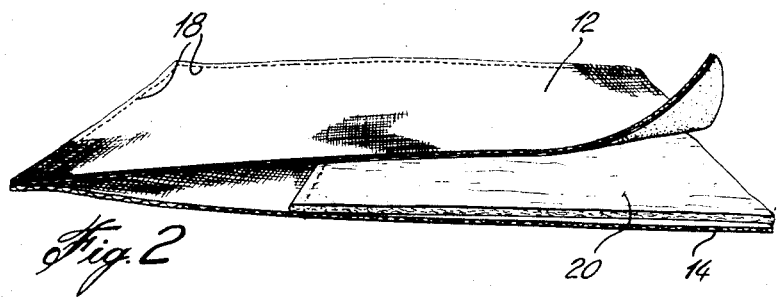
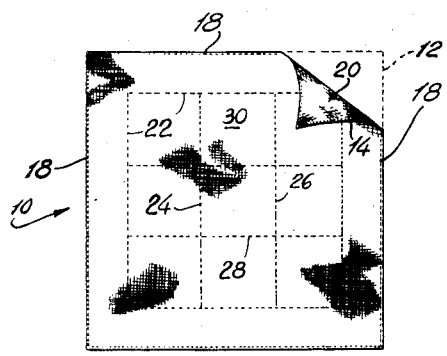
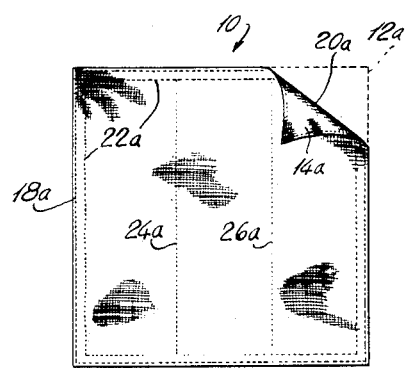

ABSORBENT BED PAD

CROSS-REFERENCE TO RELATED APPLICATIONS

This application is a continuation in U.S. application Ser. No. 334,665, filed Dec. 28, 1981, now abandoned which is a continuation of U.S. application Ser. No. 154,433, filed May 29, 1980, now abandoned.

BACKGROUND OF THE INVENTION

1. Field of the Invention

The present invention relates to an absorbent bed pad, and more particularly, to an absorbent bed pad used for hospital purposes.

2. Description of the Prior Art

In situations such as in hospitals where certain incapacitated patients might have little or no control to prevent themselves from urinating or defecating, it is customary to use an absorbent pad between the patient and the mattress of the bed in order to protect the mattress. In the case of simple impervious layer such as rubber or the like which is normally placed between the mattress and the bed linens, the mattress only is protected, but not the bed linens. Once the patient has urinated, he may be subjected to discomfort since the bed linens become wet, and there is very little capacity of absorbing the urine.

Diapers have also been developed to be worn by such patients, but these have not proven to be desirable for bed-ridden patients, since the lack of air circulation encourages bed sores or skin irritation, and leakage from the diaper will wet the linens anyway.

SUMMARY OF THE INVENTION

It is an aim of the present invention to provide as suitable improved pad which will have the capacity of absorbing and dissipating a greater amount of urine, particularly from adult patients, in order to prevent the mattress and bed linens from becoming wet and also to prevent skin irritations and bed sores to the patient.

A construction in accordance with the present invention includes an absorbent pad including a first water impervious sheet, at least one soft pervious sheet of fabric covering a centrally located area of supplemental absorbent material, the fabric sheet being stitched together with the supplemental absorbing material.

In a specific embodiment, the fabric sheet is stitched along its peripheral edges to the peripheral edges of the impervious sheet.

The advantage of such a construction is that a large pad can be provided covering a large portion of the bed surface and a soft fabric surface is exposed to the patient while the central area of the pad which has minimum stitching reduces the possibility of bed sores and/or skin irritation, is provided with an increased amount of soft absorbent material.

In a more specific embodiment of the present invention, there is provided a stitched pattern which divides the central absorbent area into square or parallel segments of equal area sufficient to prevent the materials from bunching but to minimize the occurrence of skin irritations and/or bed sores from the stitching, bunching, pleating and the like.

In a still more specific embodiment, the absorbent material may be stitched only to the peripheral edges with the fabric sheet.

BRIEF DESCRIPTION OF THE DRAWINGS

The invention will now be described with reference to the accompanying drawings which show a preferred form thereof and wherein:

FIG. 1 is a fragmentary perspective view of a proposed absorbent pad;

FIG. 2 is an enlarged fragmentary perspective view, partly in cross section, showing details of the absorbent pad of FIG. 1;

FIG. 3 is a top plan view of the absorbent bed pad shown in FIG. 1; and

FIG. 4 is a top plan view of another embodiment of the bed pad.

DESCRIPTION OF THE PREFERRED EMBODIMENTS

Referring now to the drawings, there is shown an absorbent bed pad 10 having an impervious sheet 12 made of latex bonded with cotton for stability and flexibility. The fabric layer 14 is co-extensive with the impermeable layer 12 and they are stitched at their peripheries along stitch line 18. The fabric layer 14 which can be made of a soft absorbent material covers a highly absorbent section centrally thereof, and the absorbent section is identified by the numeral 20. This absorbent section can be woven or non-woven fabric or preferably needle punched or fiber filled materials which can be loose synthetic fibers or any other type of fiber with high absorbent and quick drying characteristics. A pair of fabric layers 14 could be provided, sandwiching the fiber filled materials.

When the pad 10 is being constructed the fabric layer 14 is normally chosen to be of greater dimension than the impervious layer 12. After the first washing, the fabric layer 14 will shrink, to approximately the size of the impervious layer 12.

The fabric layer 14 is stitched peripherally of the absorbent section 20 at stitched lines 22 defining in this case a square pattern, and the stitching line 22 is intersected by means of cross stitches 24, 25, 26 and 27, which retain the absorbent material. None of the stitching lines 24, 25, 26 or 27 connect to the impervious layer 12 so as to reduce the changes of urine passing through the impervious layer which would normally be laid flat down on the bed.

FIG. 4 illustrates the pad 10 when only stitch lines 22a, 24a and 26a are provided dividing the central portion into three equal sections. The remaining numerals are the same but the numerals have been raised by the subscript "a".

In a typical example, the absorbent pad 10 measured 31"×35" while the central absorbent area measured 21"×31".

The fabric layer 14 measured 33"×38" before being applied to the periphery of impervious layer 12 which measures 31"×35". After shrinkage the fabric layer 14 is taut, without causing the pad 10 to curl or wrinkle.

In another embodiment the absorbent material is made of a mixture of fibers in the following proportions: 50% to 100% of rayon and 0% to 50% of polyester. Preferably the range should be 70% rayon and 30% polyester. It is possible to have the absorbent material extend to the peripheral stitching if the absorbent material has good enough absorption and retention.

We claim:

1. A reusable, washable absorbent bed pad having an increased urine absorption capacity comprising a first sheet of a soft previous fabric; a non-woven layer of liquid-absorbent material predominantly made up of absorbent fibers underlying at least a central portion of the first sheet, the liquid-absorbent non-woven material being chosen from a group of materials including fiberfill and needle punched artificial absorbent fibers, means fixing the layer of liquid-absorbent material only to said first sheet; and an impermeable sheet coextensive with the first sheet and stitched thereto only at the periphery of said first sheet, the first sheet and the impermeable sheet sandwiching the layer of non-woven liquid-absorbent material therebetween.

2. An absorbent bed pad as defined in claim 1, wherein the means for fixing the layer of liquid-absorbent material is a quilted stitching to the first sheet.

3. An absorbent bed pad as defined in claim 1, wherein the absorbent material is made of a mixture of fibers in the following proportions: 50% to 100% rayon and 0% to 50% polyester.

* * * * *